United States Patent [19]

Broemer et al.

[11] Patent Number: 4,617,024
[45] Date of Patent: Oct. 14, 1986

[54] AUDITORY OSSICLE PROSTHESIS AND PROCESS FOR ITS MANUFACTURE

[75] Inventors: Heinz Broemer, Wetzlar-Hermannstein; Klaüs Deutscher, Wetzlar; Henning Franek, Braunfels-Tiefenbach; Ralf Reck, Mainz-Bretzenheim, all of Fed. Rep. of Germany

[73] Assignee: Ernst Leitz Wetzlar GmbH, Wetzlar, Fed. Rep. of Germany

[21] Appl. No.: 555,347

[22] Filed: Nov. 28, 1983

[30] Foreign Application Priority Data

Mar. 26, 1982 [DE] Fed. Rep. of Germany ....... 3211209

[51] Int. Cl.⁴ .............................................. A61F 2/18
[52] U.S. Cl. .................................... 623/10; 128/92 C
[58] Field of Search ................. 3/1, 1.9, 1.91, 1.911, 3/1.913, 1.912; 128/92 C, 92 CA, 92 G

[56] References Cited

U.S. PATENT DOCUMENTS

| | | | |
|---|---|---|---|
| 3,677,795 | 7/1972 | Bokros | 3/1.9 |
| 3,909,852 | 10/1975 | Homsy | 3/1.9 |
| 3,919,723 | 11/1975 | Heimke et al. | 3/1.9 |
| 4,052,754 | 11/1977 | Homsy | 3/1.9 |
| 4,168,326 | 9/1979 | Broemer et al. | 3/1.9 |
| 4,169,292 | 10/1979 | Grote | 3/1 |
| 4,234,972 | 11/1980 | Hench et al. | 3/1.9 |

FOREIGN PATENT DOCUMENTS

| | | |
|---|---|---|
| 0064278 | 4/1982 | European Pat. Off. . |
| 0064277 | 4/1982 | European Pat. Off. . |
| 2383656 | 10/1978 | France . |
| 2025238 | 1/1980 | United Kingdom ..... 3/1.9 |
| 1562999 | 3/1980 | United Kingdom ..... 623/16 D |
| 2041759 | 9/1980 | United Kingdom ..... 623/10 |

Primary Examiner—Richard J. Apley
Assistant Examiner—David J. Isabella
Attorney, Agent, or Firm—Schwartz, Jeffery, Schwaab, Mack, Blumenthal & Evans

[57] ABSTRACT

An auditory ossicle prosthesis is described comprising a plate (1) with a groove (7) applied to its upper side and a shaft (2) eccentrically applied to its lower side. The prosthesis consists of a bioactive material and contains additionally at least in one partial area an insoluble bioinert material, which is applied mainly as a coating material in the form of an additive layer (S(+)) or a subtractive layer (S(−)). Suitable coating processes and substances are disclosed. If S(−) layers are applied, they may be exposed subsequently to a sealing and/or silanizing treatment.

13 Claims, 8 Drawing Figures

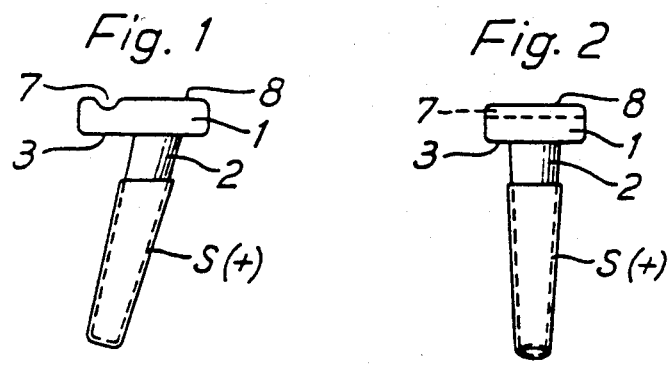
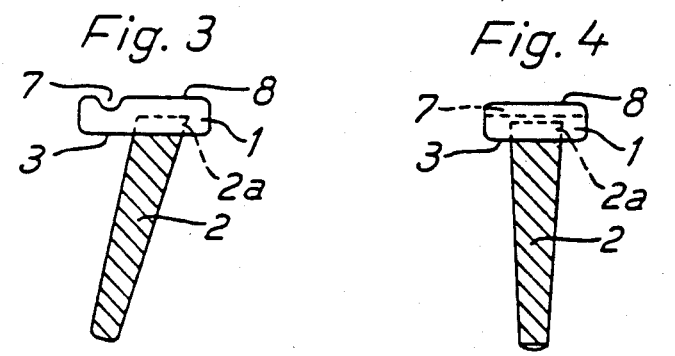
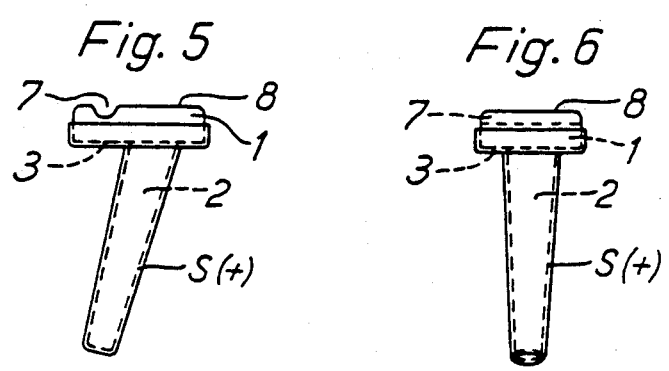
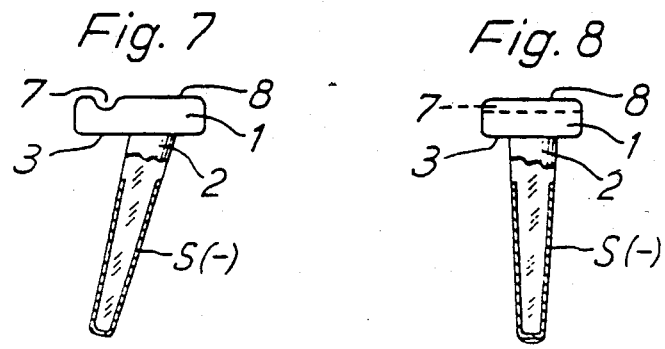

AUDITORY OSSICLE PROSTHESIS AND PROCESS FOR ITS MANUFACTURE

CROSS-REFERENCE TO RELATED APPLICATION

This application is a continuation pursuant to 35 U.S.C. 120 of our prior copending international application No. PCT/DE83/00057, which was filed on Mar. 26, 1983 and which designates the United States.

BACKGROUND OF THE INVENTION

The present invention concerns an auditory ossicle prosthesis comprising a plate with a groove on its upper surface and a shaft eccentrically applied to the underside, of the general type disclose in German Patent Application No. P 30 36 245.9-35 (corresponding to U.S. application Ser. No. 385,371, filed May 26, 1982), now U.S. Pat. No. 4,473,909 and a process for its manufacture.

Prostheses of the aforementioned type are used for the complete or partial reconstruction of the auditory ossicle tract located in the tympanum. In particular, excellent acousto-mechanical coupling may be obtained between the sound receiving tympanum and—in the absence of a functioning malleus and/or incus—the sound conducting stapes stirrup and the stapes footplate by means of the local-anatomically optimum fitting of the implant.

The decisive condition for such favorable oto-surgical results is the use of bioactive prosthesis material, in particular bioglass ceramics or bioglass.

It is known that bioactive bone replacement materials of this type have a certain surface solubility, which presumably represents a precondition necessary for the achievement of the bond between the bone and the implant. On the other hand, this particular property under especially unfavorable local anatomical conditions, such as those present when the implantation of a prosthesis takes place in soft tissue or if the prosthesis is in contact with soft tissue, may lead to a deterioration of the long term stability of the implant.

SUMMARY OF THE INVENTION

It is therefore the object of the invention to develop the partial areas of auditory ossicle prostheses made of a bioactive material, not intended to be bonded to the bone itself (implant/hard bone tissue fusion zone), so that they are completely biochemically resistant and bio-inactive. It is a further object of the invention to provide a process for the subsequent bio-inactivation of selected partial areas of auditory ossicle prostheses which are bioactive in themselves.

The object of the invention is attained in the case of prostheses of the aforementioned type in that they contain in at least one partial area an insoluble bioinert material. The object of the invention is attained further in that—beginning with a one or two piece prosthesis consisting of a bioactive material—partial areas of said prosthesis or parts of said prosthesis (plate; shaft) are exposed either to a subsequent surface treatment with the controlled application of a substance, to produce at least one additively obtained, permanently adhering protective, bioinert layer which acts in vivo as a biochemical barrier layer, or to a subsequent chemical treatment with the controlled removal or exchange of substances, to obtain subtractively a conversion (leached) layer which acts in vivo as a barrier layer.

Further objects, features and advantages of the invention will become apparent from the detailed description of preferred embodiments which follows, when considered with the attached Figures of drawing.

BRIEF DESCRIPTION OF THE DRAWINGS

The drawings schematically illustrate exemplary embodiments of the invention, wherein the representation of the lateral and front elevation of the auditory ossicle prosthesis is based on the oblique shaft arrangement with a transverse groove shown in FIGS. 1 and 2 of German Patent Application No. P 30 36 245.9-35, with the same reference symbols being selected to the extent possible.

In the drawing:

FIGS. 1 and 2 show a prosthesis with partial coating (additive layer) of the shaft;

FIGS. 3 and 4 illustrate a two-piece prosthesis consisting of a shaft made of a bioinert material and a plate made of a bioactive material;

FIGS. 5 and 6 illustrate a further embodiment, wherein the additive layer includes the entire shaft and the underside of the plate;

FIGS. 7 and 8 illustrate another embodiment with an incorporated (subtractive) layer of the shaft.

DETAILED DESCRIPTION OF PREFERRED EMBODIMENTS

The auditory ossicle prosthesis consists of a plate 1, on the upper side 8 of which is provided a groove 7, which extends eccentrically and perpendicularly to the plane of the drawing. On the underside 3 a shaft 2 is arranged eccentrically.

The prosthesis may be made in one piece of a bioactive material, as shown essentially in FIGS. 5 and 6. It is, however, also possible to compose it of two pieces, in which case either both parts—i.e. the shaft 2 and the plate 1—consist of a bioactive material or the plate is made of a bioactive and the shaft of a bioinactive, insoluble—i.e. "bioinert"—material. In the case of a two-piece form of a prosthesis the shaft 2 may be held in a bore 2a in a solid fitted setting; compare FIGS. 3 and 4. This may be obtained, for example, in that the part of the shaft 2 entering the bore 2a is custom made with a reduced tolerance and exposed immediately prior to in insertion to a localized cooling treatment. Other fitting methods, such as rivets, screws, wedges or adhesive bonding may also be used, in principle.

In FIGS. 1, 2, 5 and 6 the additively applied bioinert layer S(+) is shown. It is an essential characteristic of the present invention that bioactive material is used only in those partial surface areas of the prosthesis, which in vivo are in direct contact with osseous tissue and that the partial surface areas of the prosthesis which in vivo are in contact with soft tissue—for example epithelia—are provided with a biochemical "corrosion" protection layer, as it were, which assures a complete transport and passage barrier against any material (ion) exchange between the chemical components of the implant and the components of the physiological-biochemical body fluids.

A protective layer S(−), as shown in FIGS. 7 and 8, may also be obtained in vivo by the following method. In an auditory ossicle prosthesis consisting of a solid bioglass-ceramic material or a bioglass material, the partial surface areas which necessarily (as the result of anatomical conditions) or as selected by the surgeon (for example, in case of the lining of certain implant areas with epithelial tissue) are in permanent contact with soft tissue are chemically pretreated in such a way that aqueous acid solutions and/or aqueous salt solution in normalities between the 0.001 and 0.1 attack the originally bioglass-ceramic surface, wherein corrosive (dissolution or leaching) and exchange reactions are taking place simultaneously, with the consequence that initially a depletion and finally the complete destruction (transformation) of a phase—in particular the crystalline component or components—of the glass-ceramic composite system is obtained.

However, for the chemical attack, bases and buffer systems may also be used, which as a function of their actual chemical nature, their concentration and their pH value act in a selective manner on certain phase components of the bioglass-ceramic "composite system", thereby effecting the change of properties of the implant surface desired.

The glass-ceramic remaining after this combined chemical treatment, devoid of its apatite components, shall be designated a "residual bioglass ceramic". In its chemical properties it is insoluble, nonporous, and it blocks any transport of ions; with respect to its biochemical and physiological effects, it is bio-inactive, i.e. bio-"inert", and with respect to its mechanical properties, it is abrasion resistant and tightly adherent to the core material of the prosthesis.

If necessary, the layer S(−) obtained in this manner may be thermally densified or sealed. Furthermore, a silanizing layer may be applied additionally.

If, as the result of a given pathological condition, the end of the prosthesis shaft facing away from the prosthesis plate 1 is in direct osseous contact with a remaining portion of an auditory ossicle (stapes head), the bioinert protective layer S(+) or S(−) should be first removed in the contact area, in order to obtain optimum fusion conditions in this location, depending on the requirements of the otolaryngology surgeon. On the upper side of the plate 8, prior to the implantation process proper, the development of a quasi-compact osseous lamellar layer is induced by the application of a granular, autologous bone meal, which serves as an intermediate contact zone between the upper side of the plate of the auditory ossicle prosthesis and the tympanum.

We claim:

1. An auditory ossicle prosthesis, comprising: a generally planar plate; a shaft attached eccentrically to the underside of said plate; and a groove provided in the top side of the plate, wherein the plate and attached shaft have a mirror symmetrical configuration with respect to at least one symmetry plane perpendicular to the plane of the plate and passing through the shaft; the shaft is attached so that its contact surface with the plate is located on the symmetry plane of the plate, but is removed by at least one-half of the diameter of the shaft from the boundary area of the plate; the groove is arranged on the top side of the plate in its front half and is aligned perpendicular to the symmetry plane of the prosthesis; and wherein at least one of said plate and said shaft is comprised of a bioactive material and the prosthesis comprising at least one partial area of said bioactive material which has been selectively rendered bioinactive and which comprises an insoluble bioinert material for preventing ion exchange in vivo between the bioactive material and body fluids.

2. An auditory ossicle prosthesis according to claim 1, comprising in at least one partial surface area an insoluble, bioinert material.

3. An auditory ossicle prosthesis according to claim 1, wherein said partial area comprises a coating of an insoluble, bioinert material.

4. An auditory ossicle prosthesis according to claim 3, wherein the coating comprises at least one additively applied protective layer with a thickness between about 0.25 and 10 microns.

5. An auditory ossicle prosthesis according to claim 3, wherein the coating comprises at least one subtractively produced conversion layer with a thickness between about 0.25 and 5 microns.

6. An auditory ossicle prosthesis according to claim 3, wherein the coating comprises at least one conversion layer produced on the prosthesis and at least one additively applied protective layer applied on said conversion layer.

7. An auditory ossicle prosthesis according to claim 1, wherein the prosthesis shaft comprises at least in its mantle area in insoluble bioinert material.

8. An auditory ossicle prosthesis according to claim 1, wherein only the plate, at least on its upper side, is comprised of a bioactive material.

9. An auditory ossicle prosthesis according to claim 1, wherein the plate comprises a bioactive solid material and the shaft comprises a bioinert solid material.

10. An auditory ossicle prosthesis according to claim 1, wherein the plate comprises at least in its upper surface area a bioactive material and the shaft comprises at least in its mantle area an insoluble bioinert material.

11. An auditory ossicle prosthesis according to claim 1, wherein the bioinert material or the bioinert layer comprises at least one of the following substances:
   (a) a metal comprising gold, platinum or titanium, or a metal alloy;
   (b) carbon in the form of pyrolytic carbon (graphite); or a carbon compound comprising silicon carbide (SiC), titanium carbide (TiC) or boron carbide ($B_4C$);
   (c) a ceramic material comprising hexagonal boron nitride (BN), titanium nitride (TiN) or silicon nitride ($Si_3N_4$);
   (d) a partially crystalline inorganic composite system comprising an enamel;
   (e) an inorganic single component glass or a multiple component glass; or
   (f) an oxide comprising titanium dioxide ($TiO_2$), zirconium dioxide ($ZrO_2$) or aluminum oxide ($Al_2O_3$).

12. An auditory ossicle prosthesis according to claim 1, wherein the bioinert material or the bioinert layer comprises an apatite-free residual-bioglass ceramic or residual-bioceramic or residual-bioglass, with or without a silane layer.

13. An auditory ossicle prosthesis according to claim 1, wherein the bioactive material comprises a bioglass or a bioglass-ceramic.

* * * * *